US007368256B2

(12) United States Patent
Schmechel et al.

(10) Patent No.: US 7,368,256 B2
(45) Date of Patent: May 6, 2008

(54) **ANTIBODIES AGAINST *STACHYBOTRYS CHARTARUM* AND METHODS FOR THEIR USE**

(75) Inventors: Detlef Schmechel, Morgantown, WV (US); Daniel M. Lewis, Kingwood, WV (US)

(73) Assignee: United States of America as represented by the Secretary of the Department of Health and Human Services, Centers for Disease Control and Prevention, Washington, DC (US)

( * ) Notice: Subject to any disclaimer, the term of this patent is extended or adjusted under 35 U.S.C. 154(b) by 500 days.

(21) Appl. No.: 10/483,921

(22) PCT Filed: Aug. 9, 2002

(86) PCT No.: PCT/US02/25493

§ 371 (c)(1),
(2), (4) Date: Jan. 14, 2004

(87) PCT Pub. No.: WO03/016352

PCT Pub. Date: Feb. 27, 2003

(65) Prior Publication Data

US 2004/0185051 A1    Sep. 23, 2004

Related U.S. Application Data

(60) Provisional application No. 60/311,458, filed on Aug. 10, 2001.

(51) Int. Cl.
*G01N 33/554*    (2006.01)
*C01K 16/00*    (2006.01)
*C12P 21/08*    (2006.01)

(52) U.S. Cl. .................... 435/7.32; 435/332; 436/518; 530/388.2

(58) Field of Classification Search .................... None
See application file for complete search history.

(56) References Cited

U.S. PATENT DOCUMENTS

| 4,281,061 | A | * | 7/1981 | Zuk et al. ..................... 435/7.9 |
| 5,558,997 | A | | 9/1996 | Petersen et al. |
| 5,804,393 | A | | 9/1998 | Geiser et al. |
| 5,895,922 | A | | 4/1999 | Ho |
| 2003/0206927 | A1 | * | 11/2003 | Vesper ..................... 424/274.1 |

FOREIGN PATENT DOCUMENTS

| WO | WO 01/11366 A1 | 2/2001 |
| WO | WO 01/29558 A1 | 4/2001 |

OTHER PUBLICATIONS

Johanning et al (International Archives of Occupational and Environmental Health, 68(4):207-218, 1996).*
Calbiochem 1998 General catalog (pp. 626-629).*
Lander et al., "Serum IgE Specific to Indoor Moulds, Measured by Basophil Histamine Release, is Associated With Building-Related Symptoms in Damp Buildings," *Inflamm. Res.* 50:227-231 (2001).
Raunio et al., "Preliminary Description of Antigenic Components Characteristic of *Stachybotrys chartarum*," *Env. Res.* 85:246-255 (2001).
Schemchel et al., "The Production of Species-Specific Monoclonal Antibodies (Mabs) Against with Allergenic and Toxigenic Fungus *Stachybotrys chartarum*," FASEB Journal, Mar. 7, 2001, vol. 15, No. 4, p. A662, see abstract No. 523.1.

* cited by examiner

*Primary Examiner*—Patricia A. Duffy
(74) *Attorney, Agent, or Firm*—Klarquist Sparkman, LLP; Paula A. DeGrandis (57) ABSTRACT

Antibodies to various fungal antigens are disclosed, including monoclonal antibody 9B4 that selectively binds an antigen of *Stachybotrys chartarum* spores not found in *Stachybotrys chartarum* mycelium. The antibodies may be used in a variety of methods, such as detecting the presence of fungal antigens in the environment or within a sample obtained from an animal or plant, or testing the effectiveness of an agent in binding an antigen.

19 Claims, 6 Drawing Sheets

ANTIBODIES AGAINST *STACHYBOTRYS CHARTARUM* AND METHODS FOR THEIR USE

This is a national stage under 35 U.S.C. §371 of International Application No. PCT/US02/25493, filed Aug. 9, 2002, and claims the benefit of U.S. Provisional Patent Application No. 60/311,458, filed Aug. 10, 2001.

FIELD

This invention relates to binding agents, such as antibodies, that bind to target molecules, including cellular components of fungi.

BACKGROUND

Certain fungi found in indoor environments, including homes and businesses, may cause adverse health effects in people and animals by provoking allergic reactions, causing infection, or releasing toxic substances. Recently, some attention has focused on the fungus *Stachybotrys chartarum*, which grows in moist indoor environments. Exposure to this fungus has been implicated in respiratory, dermatological, gastrointestinal, and central nervous system disorders in humans and a variety of animals. See, e.g., Fung, F., et al., *Clinical Toxicology* 36:79-86 (1998); Robbins, C. A., et al., *Applied Occupational and Environmental Hygiene* 15:773-84 (2000). For example, it has been suggested that *Stachybotrys chartarum* may be associated with "sick building syndrome," an occupational condition in which workers are sickened by environmental toxins or pathogens. Craner, J., in: *Bioaerosols, Fungi and Mycotoxins: Health Effects, Assessment, Prevention and Control*, Johanning, E. (Ed.), (Eastern New York Occupational and Environmental Health Center, Albany, N.Y., 1999), pp. 146-157.

Exposure to the toxic substances, such as trichothecenes, or allergens produced by *Stachybotrys chartarum* is implicated in some respiratory disorders, including inflammation and hemorrhage of the lungs, and also may increase disease susceptibility in exposed subjects by affecting the inflammatory and immune responses after exposure. See, e.g., Dearborn, D. G., et al., *Environmental Health Perspectives* 107:495-99 (1999); Flappan, S. M., et al., *Environmental Health Perspectives* 107:927-930 (1999); Elidemir, O., *Pediatrics* 104:964-66 (1999); and Pitt, J. I., *British Medical Bulletin* 56: 184-92 (2000). However, the exact role of *Stachybotrys chartarum* in causing these adverse health effects is not well known and has been controversial, especially regarding human susceptibility to *Stachybotrys chartarum*.

Accurate and precise monitoring methods are needed to better understand and analyze the role of *Stachybotrys chartarum* in certain diseases or conditions and the relevance of this fungus in causing or contributing to such health effects. Current methods of detecting this fungus rely on spore counts and cultivation of samples, which can be time-consuming and labor-intensive, or use chromatographic detection of specific mycotoxins, which can be insensitive and often requires specialized equipment. Therefore, a need exists for a method of assessing exposure to *Stachybotrys chartarum* that is rapid, accurate, and efficient.

If available, an antibody that binds to an antigen on a fungus may be used to detect some fungi. An antibody-antigen complex, formed when an antibody binds to an antigen, may be detected using a variety of techniques, such as the enzyme linked immunosorbent assay (ELISA), particle immunostaining, or fluorescence-based image analysis. For example, monoclonal antibodies against fungal allergens expressed by *Alternaria alternata* and several *Aspergillus* and *Penicillium* species have been used to identify and characterize environmental contamination. Chapman, M. D., et al., *Clinical Reviews in Allergy and Immunology* 18:285-300 (2000). The application of these monoclonal antibodies for measuring exposure was compromised by their cross-reactivity with other fungal species, variability or lack of essential expression of allergens recognized by the antibodies, or the lack of assay sensitivity due to low level production of allergens per unit biomass. Mitakakis, T. Z., et al., *Journal of Allergy and Clinical Immunology* 107:388-90 (2001); Vailes, L., et al., *Journal of Allergy and Clinical Immunology* 107:641-46 (2001). However, antibodies to *Stachybotrys* species, such as *Stachybotrys chartarum*, and associated methods of detecting these fungi were not previously known.

SUMMARY

Disclosed are antibodies to antigens produced by fungi commonly found in indoor environments (see Table 1), such as antibodies to an antigen of *Stachybotrys chartarum*, including antigens secreted by *Stachybotrys chartarum*. Particular examples of such antibodies include monoclonal antibody (Mab) 9B4, which binds an antigen of *Stachybotrys chartarum* spores, or other antibodies that recognize an antigen to which 9B4 specifically binds. Mab 9B4 does not react with spores or mycelium of other fungi commonly found in indoor environments, including multiple species and/or isolates of *Alternaria, Aspergillus, Aureobasidium, Botrytis, Cladosporium, Chaetomium, Curvularia, Fusarium, Memnoniella, Mucor, Myrothecium, Paecilomyces, Penicillium, Rhizopus, Scopulariopsis, Trichoderma, Ulocladium* and *Wallemia* fungal genera, including those identified in FIGS. 1-6. Mab 9B4 also does not react with spores of other *Stachybotrys* species such as *S. albipes, S. bisbyi, S. cylindiospora, S. echinata, S. kanipalenisis, S. microspora, S. nephrospora* or *S. subsimplex*. Hence, Mab 9B4 can be considered species-specific for spores of *Stachybotrys chartarum*. Other particular examples of antibodies include Mabs 1D4, 3B2, 4E12, 9F9 and 10A5, which react with spores and/or mycelium of multiple fungal species, including *Stachybotrys chartarum*.

Monoclonal antibody 9B4 provides a specific test for the presence of, or exposure to, *Stachybotrys chartarum* spores. Cell lines producing these antibodies, such as a hybridoma that produces the 9B4 monoclonal antibody, and labeled antibodies, such as antibodies carrying a radiolabel, biotin, or a fluorescent, calorimetric, or luminescent label, also are disclosed.

The antibodies may be used to identify and detect the presence of a fungus within a sample obtained from the environment (e.g., soil, water, dust, bulk material, and air samples), a plant, or an animal. Additionally, since antigen may remain on or within an environmental locus, animal, or plant after being contacted by a fungus, exposure to the fungus may be detected even if the fungus later disintegrates or disappears. The antibodies may be used to detect viable or dead fungi, fungal components, or soluble components, such as actively secreted or passively released fungal products or immune complexes. Such fragments or components may be detected even after the physical or chemical breakdown of a fungus.

To detect exposure to the fungus, an interaction between the antigen and antibody is detected. In some instances, the sample is contacted with an antibody, and detection of an antibody-antigen complex indicates the presence of antigen in the sample, either an antigen presently associated with a fungus or an antigen that remained in the sample after the fungus contacted the sample. In other instances, the antibody is used to immunoprecipitate the corresponding antigen, and the isolated antigen is used to screen a sample for the presence of other antibodies to the antigen. For example, monoclonal antibody 9B4 may be used to isolate its cognate antigen, and that antigen may be used to detect exposure to *Stachybotrys chartarum* spores in animals by screening a blood sample for reactive antibodies.

The antibody also may be part of a kit for detecting a fungus or other antibodies, such as a kit containing monoclonal antibody 9B4 for detecting *Stachybotrys chartarum* spores. For example, Mab 9B4 may be part of a kit to detect spores of *S. chartarum* in environmental samples or to detect antibodies of similar specificity in animal samples.

The antibodies also may be used to test the effectiveness of an agent in binding an antigen. In such embodiments, an antibody is mixed with an antigen and the agent, and antibody-antigen binding in the presence of the agent is compared to some reference standard or control. For example, monoclonal antibody 9B4 may be mixed with *Stachybotrys chartarum* spores and an agent; if 9B4-spore binding in the presence of the agent is less than in a negative control (i.e., binding in the absence of the agent), then the agent interferes with the 9B4-spore binding and may effectively bind the same antigen as 9B4.

The detection of an immune complex formed between a Mab and its corresponding fungal antigen, or the inhibition of the binding of a Mab to its antigen by competitive or blocking antibodies or antigens, may be accomplished by several techniques. Such analytical techniques include, but are not limited to, assays using labeled or unlabeled reagents or antibodies. If labeled reagents and/or antibodies are used, the label may be a radioisotope, enzyme, metal, or a fluorescent, phosphorescent or chemiluminescent compound. Such assays include, for example, competitive and non-competitive homogenous and heterogenous enzyme-linked immunosorbent assays (ELISA) as symmetrical or asymmetrical direct or indirect detection formats; enzyme-linked immunospot assays (ELISPOT); radioallergosorbent tests (RAST); fluorescent tests, such as used in fluorescent microscopy and flow cytometry; Western, grid, dot or tissue blots; dip-stick assays; halogen assays; or protein arrays including antibody arrays. Other analytical techniques include immune complex-based assays such as immunodiffusion, precipitation, coagulation, agglutination and hemagglutination techniques as well as tests based on turbidimetry or nephelometry.

The following abbreviations for fungal species are used herein; the numbers following each species name indicate the spore concentrations per well used in ELISA: Aal—*Alternaria alternata*, 6,750; Aca—*Aspergillus candidus*, 115,000; Acl—*Aspergillus clavatus*, 875,000; Afl—*Aspergillus flavus*, 267,000; Afu—*Aspergillus fumigatus*, 1,000,000; Ani—*Aspergillus niger*, 458,750; Are—*Aspergillus repens*, 61,500; Ars—*Aspergillus restrictus*, 38,000; Asy—*Aspergillus sydowii*, 875,000; Ate—*Aspergillus terreus*, 1,000,000; Ave—*Aspergillus versicolor*, 712,000; Apu—*Aureobasidium pullulans*, 961,250; Bci—*Botrytis cinerea*, culture surface washing only; Ccl—*Cladosporium cladosporioides*, 371,250; Che—*Cladosporium herbarum*, 807,500; Csp—*Cladosporium sphaerospermum*, 60,500; Cgl—*Chaetomium globosum*, culture surface washing only; Clu—*Curvularia lunata*, culture surface washing only; Eam—*Eurotium amstelodami*, 29,750; Eni—*Epicoccum nigrum*, 5,750; Fcu—*Fusarium culmorum*, 389; Fmo—*Fusarium moniliforme*, 1,300,000; Fox—*Fusarium oxysporum*, 845,000; Fso—*Fusarium solani*, 8,750; Ftr—*Fusarium tricinctum*, 34,000; Gca—*Geotrichum candidum*, 1,200,000; Mec—*Memnoniella echinata*, 262,500; Mra—*Mucor ramannianus*, 26,750; Mve—*Myrothecium verrucaria*, 40,750; Pbr—*Penicillium brevicompactum*, 1,000,000; Pch—*Penicillium chrysogenum*, 633,333; Pci—Penicillium citrinum, 1,000,000; Pex—*Penicillium expansum*, 1,000,000; Pis—*Penicillium islandicum*, 521,250; Ppu—*Penicillium purpurogenum*, 30,000; Pro—*Penicillium roqueforti*, 466,250; Pva—*Paecilomyces variotii*, 535,000; Pve—Penicillium variabile, 1,000,000; Rst—*Rhizopus stolonifer*, 481,000; Sal—*Stachybotrys albipes*, 6,500; Sbi—*Stachybotrys bisbyi*, 6,250; Sbr—*Scopulariopsis brumptii*, 47,500; Sch 1-14—*Stachybotrys chartarum* isolates 1-14, 71,750; 33,000; 62,000; 89,250; 32,500; 29,500; 78,000; 36,250; 64,750; 66,250; 21,500; 79,250; 43,500; 103,000 respectively; Scy—*Stachybotrys cylindrospora*, 35,750; See—*Stachybotrys echinata*, 109,000; Ska—*Stachybotrys kampalensis*, 2,000; Smi—*Stachybotrys microspora*, 27,000; Sne—*Stachybotrys nephrospora*, 22,500; Ssu—*Stachybotrys subsimplex*, 2,000; Tha—*Trichoderma harzianum*, 1,000,000; Uch—*Ulocladium chartarum*, 31,500; Wse—*Wallemia sebi*, 205,250.

DETAILED DESCRIPTION

Antibodies that selectively bind to antigens produced by fungi commonly found in indoor environments are disclosed. In some embodiments, a monoclonal antibody selectively binds an antigen produced by *Stachybotrys chartarum* (Ehrenb.) Hughes (Syn. *Stachybotrys atra* Corda, *Stachybotrys alternans* Bonord), such as monoclonal antibody 9B4, which selectively binds to the spores, but not the mycelium, of *Stachybotrys chartarum*.

Abbreviations
  ATCC: American Type Culture Collection
  BSA: bovine serum albumin
  CCB: carbonate coating buffer
  CDR: complementarity-determining region
  CSN: culture supernatant
  DMEM: Dulbecco's Modified Eagle Medium
  ELISA: enzyme-linked immunosorbent assays ELISPOT: enzyme-linked immunospot assays
KLH: keyhole limpet hemocyanin
Mab: monoclonal antibody
PBS: phosphate buffered saline
PBST: phosphate buffered saline supplemented with 0.05% Tween 20
PCR: polymerase chain reaction
RAST: radioallergosorbent tests
RT: room temperature Explanations of Terms The following explanations of terms are provided to better illustrate certain features of the invention and to facilitate review of the embodiments described herein. Explanations of common terms also can be found in Goldsby, R. A. et al., *Kuby Immunology*, 4$^{th}$ edition, W. H. Freeman & Co.: New York, 2000; Janeway, C. (Editor) and Travers, P., *Immunobiology*, 5$^{th}$ edition, Garland Pub: New York, 2001; and Harlow, E., and Lane, D., *Using Antibodies: A Laboratory Manual*, Cold Spring Harbor Laboratory Press: Cold Spring Harbor, 1998.

As used herein, the singular forms "a," "an," and "the," refer to both the singular as well as plural, unless the context clearly indicates otherwise. For example, the term "an antibody" includes single or plural antibodies and can be considered equivalent to the phrase "at least one antibody."

The term "or" refers to a single element of stated alternative elements or a combination of two or more elements. For example, the phrase "a monoclonal or polyclonal antibody" refers to a monoclonal antibody, a polyclonal antibody, or both a monoclonal and a polyclonal antibody.

As used herein, "comprises" means "includes." Thus, "comprising an antibody and antigen" means "including an antibody and antigen," without excluding additional elements.

Animal. A living multicellular vertebrate organism, including mammals, fish, and birds. A "mammal" includes both human and non-human mammals. Similarly, the term "subject" includes both human and veterinary subjects.

Antibody. Serum protein formed in response to immunization. An immunoglobin molecule that has an amino acid sequence by virtue of which it interacts with the antigen that induced its synthesis or with related antigens.

Antigen. A substance capable of inducing a specific humoral or cellular immune response and capable of reacting with the products of that response (i.e., specific antibodies) or which can be bound by preformed antibodies. Those antigens capable of inducing antibody production are called "immunogens." Antigens can be soluble molecules such as proteins, lipids, carbohydrates, or nucleic acids; or particulates such as bacteria, virus, or fungi, as whole cells, whole particles, or fragments thereof. Antigens can have complex surfaces and can express multiple unique antigenic determinants or epitopes. An antigen expressing different independent epitopes is said to be multi-determinant, while an antigen expressing multiple copies of a given epitope is said to be multivalent.

Antigens of *Stachybotrys chartarum* can be intracellular or secreted into the environment by viable propagules, or released by disintegrating non-viable propagules. Examples of such antigens include structural proteins, cell-surface proteins, secreted proteins, and fragments thereof.

Binding reaction. Occurs when a binding agent (such as an antibody) interacts with its target (such as an antigen). In some cases, a binding reaction occurs when two structurally and/or energetically complementary molecular surfaces react to form a ligand-receptor complex with characteristic specificity and affinity. For example, a monoclonal antibody can undergo a binding reaction with its cognate antigen to form an antigen-antibody complex, also called an immune complex. Thus, a binding reaction can be referred to as a "complexing reaction."

An agent that "selectively" binds to a particular target exhibits some preference for its target over other similar targets. Some antibodies (both monoclonal and polyclonal) can discriminate between closely related epitopes and also can distinguish between different antigens, if those antigens express epitopes that are not shared by other antigens. As one non-limiting example, Mab 4E12 reacts with an epitope that is expressed by 15 out of 52 (29%) fungal species tested. See Table 2.

An agent that "specifically" binds to a particular target binds substantially only to a defined target. As used herein, a specific binding agent includes both monoclonal and polyclonal antibodies. As one non-limiting example, monoclonal antibody 9B4 specifically binds to an antigen of *Stachybotrys chartarum* spores that is not found in either *Stachybotrys chartarum* mycelium or spores or mycelia of other fungal species tested, including other Stachybotrys species. See Table 2.

Epitope. The local portion of an antigen recognized by a corresponding antibody, also called an "antigenic determinant" or "antibody binding site." An epitope is any antigenic determinant on an antigen to which the paratope of an antibody binds. Epitopic determinants can consist of chemically active surface groupings of molecules, such as amino acids or sugar side chains, and can have specific three-dimensional structural characteristics and specific charge characteristics.

Fungus. Living, single-celled and multicellular organisms belonging to Kingdom Fungi. Characterized by a lack of chlorophyll and presence of chitinous cell walls in some species. May be multinucleated.

Hybridoma. A cell line or culture that secretes a homogenous population of monoclonal antibodies. Hybridomas are hybrid cells resulting from the fusion of a myeloma (tumor cell), which confers immortality, and an antibody-producing cell, which confers antibody specificity onto the hybridoma. One specific, non-limiting example is the hybridoma capable of producing Mab 9B4 that was deposited on Aug. 9, 2002 with the American Type Culture Collection (ATCC, Manassas, Va.) under ATCC accession number PTA-4582.

Isolated. An "isolated" biological component—such as a molecule, antibody, nucleic acid, or cellular organelle—has been substantially separated or purified away from other biological components of the organism in which the molecule, antibody, nucleic acid or cellular organelle naturally occurs. The term "isolated" thus encompasses antibodies purified by standard protein purification methods. The term "isolated" also embraces antibodies prepared by recombinant expression in a host cell and chemically synthesized antibodies.

Label. A chemical group attached to an antigen, antibody or other molecule to facilitate its detection. An antigen, antibody or other molecule may be labeled for direct detection, such as by methods described in Harlow and Lane (1998). Suitable labels include, but are not limited to, an enzyme, a radiolabel, a fluorescent label, a colorimetric label, a luminescent label, or biotin, and may be chosen based on such functions as availability of detection methods, availability of equipment, affinity of the label and labeled molecule, or degree of interference on the activity of the labeled molecule.

Monoclonal antibody (Mab). Identical antibodies derived from a single plasma cell, antibody-secreting cell, or a clone of cells thereof, that demonstrate specific affinity for certain antigen epitopes. A monoclonal antibody can be a protein synthesized in pure form by a single population of cells, such as being secreted by a hybridoma. The term "oligoclonal antibodies" or "antibody cocktail" refers to a predetermined mixture of distinct monoclonal antibodies. Also included is any antibody derivative based on any Mab disclosed herein, such as proteolytic fragments including, but not restricted to, Fab, Fab', F(ab')$_2$, Fv, Fd, or Fb fragments or any recombinant reagent based on the nucleotide or amino acid sequences of the immunoglobulin heavy or light chains.

In contrast, polyclonal antibodies, or immune sera, are a mixture of different antibodies with specificities for independent epitopes expressed by an antigen. Polyclonal antibodies are thus a diverse population of antibodies secreted by all antigen-reactive plasma cells during an immune response.

Nucleotide. A monomer composed of a sugar moiety, phosphate group, and an amine base, such as a pyrimidine, purine, or synthetic analogs thereof. A nucleotide is one monomer in a polynucleotide, such as a nucleic acid molecule. A nucleic acid sequence refers to the sequence of bases in a polynucleotide.

Polyclonal antibody. A mixture of different antibodies purified from hyperimmune serum. Polyclonal antibodies can be produced by several different methods, such as those described in Green et al., in: *Immunochemical Protocols* Manson, M. (Ed.), Humana Press, 1992, pp. 1-5; and Coligan et al., in: *Current Protocols in Immunology*, Coligan, J. E. et al. (Eds), Wiley and Sons, New York, 1992, section 2.4.1.

Polypeptide. A polymer in which the monomers are amino acid residues joined together through amide bonds. When the amino acids are alpha-amino acids, either the L-optical isomer or the D-optical isomer can be used. A "protein" may be composed of a single polypeptide molecule, or may be composed of plural polypeptide subunits.

The terms "polypeptide" and "protein" encompass any amino acid sequence and include modified sequences, such as glycoproteins. The term "polypeptide" encompasses naturally occurring proteins, as well as those that are recombinantly or synthetically produced.

A "fragment" of a polypeptide refers to a portion of a polypeptide that exhibits at least one useful epitope. The term "functional fragments" of a polypeptide refers to all fragments of a polypeptide that retain an activity of the polypeptide, such as the ability to bind a particular fungus or range of fungi. Biologically functional fragments, for example, can vary in size from a polypeptide fragment as small as an epitope capable of binding an antibody molecule to a large polypeptide capable of participating in the characteristic induction or programming of phenotypic changes within a cell.

Therapeutic agent. A substance that demonstrates some therapeutic effect by restoring or maintaining health, such as by alleviating the symptoms associated with a disease or physiological disorder, or interfering with a pathophysiological process that leads to a disease or its progression. In some instances, the therapeutic agent is an antibody, a chemical or pharmaceutical compound, or a nucleic acid molecule. A therapeutic agent can be an antifungal agent—an agent effective against fungal infections and destructive to fungi or capable of suppressing their growth or reproduction—or an antitoxin. As one non-limiting example, the therapeutic agent is an antitoxin to the toxin produced by *Stachybotrys chartarum* suitable for administration to humans.

Antibodies

Polyclonal and monoclonal antibodies against various fungal antigens may be produced using cell lines, such as hybridomas. In some embodiments, an antibody is produced by repeatedly immunizing a mammal, such as a mouse, with a target antigen until an immune response in the mammal is detected. For example, antibody production in a mouse can be verified by collecting and analyzing serum samples by ELISA. After the mammal is sacrificed, a single cell suspension is prepared from its spleen. Individual splenocytes, including many antigen-reactive plasma cells, are then immortalized by cell fusion with a myeloma cell line. The successfully fused cells (hybridomas) are cloned by dilution with aliquots placed in wells of a microtiter plate for culture growth, the clones are screened for production of antibody to the antigen, and antibody is isolated from the positive cloned hybridomas. For example, hybridomas may be aliquoted into wells of 96-well ELISA plates and, after about 10-14 days of cultivation in selective medium culture, supernatants of individual wells with cell growth are tested for the presence of target antigen-specific antibodies using a screening technique; cells of positive wells are then cloned twice by limiting dilution in order to ensure monoclonality of the resulting hybridoma. Techniques for producing and isolating monoclonal antibodies are described in detail in various references, such as in *Monoclonal antibodies—Production, Engineering and Clinical Applications*, Ritter, M. A., and Ladyman, H. M. (Eds.). Cambridge University Press, 1995*; Basic Methods in Antibody Production and Characterization*, Howard, G. C., and Bethell, D. R. (Eds.), CRC Press, 2001*; Diagnostic and Therapeutic Antibodies*, George, A. J. T., and Urch, C. E. (Eds.), Humana Press, 2000; and Harlow, E., and Lane, D. (Eds.), 1998.

Fungal antigens used to stimulate antibody production can be obtained from whole cells; fragments of cells; surface washings; or secreted, released, or extracted cellular molecules. For example, fungal cells (from spores or mycelia) can be solubilized and injected into an animal. Antibodies also can be prepared using an intact polypeptide or fragments containing small peptides of interest as the immunizing antigen. The polypeptide or protein used to immunize an animal may be derived from translated cDNA or chemical synthesis and can be conjugated to a carrier protein, if desired. Commonly used carrier proteins include keyhole limpet hemocyanin (KLH), thyroglobulin, bovine serum albumin (BSA), and tetanus toxoid.

Any animal having an immune system can be used in antibody production, such as rats, hamsters, pigs, felines, and primates, including chimpanzees, baboons, and humans.

As described in Example 1, a hybridoma may be produced by fusing hyperimmune spleen cells with SP2/0-AG14 myeloma cells using standard techniques, though monoclonal antibodies may be produced using other myelomas.

Once a cell line is produced, that cell line is cultured for a period of time, and each culture supernatant is screened against a target fungus to determine if the cell line produces a reactive antibody. A number of immunoassay techniques can be used to screen the culture supernatants, such as competitive and non-competitive homogenous and heterogenous enzyme-linked immunosorbent assays (ELISA) as symmetrical or asymmetrical direct or indirect detection formats; enzyme-linked immunospot assays (ELISPOT); radioallergosorbent tests (RAST); fluorescent tests, such as used in fluorescent microscopy and flow cytometry; Western, grid, dot or tissue blots; dip-stick assays; halogen assays; or antibody arrays. See, e.g., O'Meara, T. and Tovey, E., Clinical Reviews in Allergy and Immunology, 18:341-95 (2000); Sambrook et al., (2001), Appendix 9; Simonnet, F., and Guilloteau, D., in: *Methods of Immunological Analysis*, Masseyeff, R. F., et al. (Eds.), VCH, New York, 1993, pp. 270-388. Other analytical techniques include immune complex-based assays such as immunodiffusion, precipitation, coagulation, agglutination, and hemagglutination techniques, as well as tests based on turbidimetry or nephelometry.

A positive reaction indicates that the antibody produced by a particular cell line binds to or complexes with an antigen produced by a particular target fungus. Positive cultures are subcloned and developed by in vitro culture over long periods of time into stable cell lines that produce antibodies.

Monoclonal antibodies can be isolated from hybridoma cultures by a variety of methods, including affinity chromatography with Protein-A Sepharose, size-exclusion chromatography, and ion-exchange chromatography. Other purification methods include binding to and elution from a matrix containing the antigen to which the antibodies were raised that is bound to some substrate. See, e.g., Coligan et al., sections 2.7.1-2.7.12 and sections 2.9.1-2.9.3 (1992); Barnes et al., in: *Methods in Molecular Biology*, Vol. 10, Humana Press 1992; pp. 79-104; Coligan et al., *Current Protocols Immunology*, Wiley Interscience, 1991, Unit 9.

Particular antibodies can be selected based on the fungal antigens to which they bind. Generally, an animal is immunized with a fungal antigen, which may itself be preselected, and antibody-producing cells from that animal are used as a source for producing monoclonal or polyclonal antibodies. The resulting antibodies are isolated and screened for binding activity with various fungi, and particular antibodies are selected based on their binding patterns. For example, monoclonal antibodies that selectively or specifically bind *Stachybotrys chartarum* antigens can be produced by hybridomas resulting from antibody-producing cells obtained from animals immunized with *Stachybotrys chartarum* antigens, such as antigens from *Stachybotrys chartarum* spores, mycelia, or fragments or molecules thereof. Examples 1-3 below describe in detail how to produce a monoclonal antibody (9B4) that specifically binds to an antigen of *Stachybotrys chartarum* spores. However, the techniques described in Examples 1-3 can be modified to produce other monoclonal antibodies that, like 9B4, specifically bind an antigen of *Stachybotrys chartarum* spores. Additionally, the techniques can be modified to produce antibodies that specifically (or selectively) bind an antigen of another fungal species or part of a fungus.

Antibodies can be multiplied in vitro and in vivo. Multiplication in vitro can be carried out in suitable culture media, such as Dulbecco's Modified Eagle Medium or RPMI 1640 medium, optionally supplemented by a mammalian serum, such as fetal calf serum, or trace elements and growth-sustaining supplements, such as normal mouse peritoneal exudate cells, spleen cells, thymocytes, or bone marrow macrophages. Production in vitro provides relatively pure antibody preparations and can be scaled to yield large amounts of the desired antibodies. Large scale hybridoma cultivation can be carried out by homogenous suspension culture in an airlift reactor, in a continuous stirrer reactor, or in immobilized or entrapped cell culture.

Multiplication in vivo can be carried out by injecting cell clones into mammals histocompatible with the parent cells, such as syngeneic mice, to cause growth of antibody-producing tumors. Optionally, the animals can be primed with a hydrocarbon, especially oils, such as pristane (tetramethylpentadecane), prior to injection. After one to three weeks, the desired antibody is recovered from the body fluid of the animal.

An antibody also can be derived from a non-human primate antibody. For example, techniques for raising therapeutically useful antibodies in baboons can be found in Goldenberg et al., International Patent Publication WO 91/11465, 1991, and Losman et al., *Int. J. Cancer* 46:310 (1990).

Antibodies can be derived from a human monoclonal antibody. Such antibodies are obtained from a transgenic vertebrate organism, such as a mouse, that has been genetically engineered to produce a human antibody in response to antigenic challenge. Elements of the human heavy and light chain loci are introduced into strains of these organisms derived from embryonic stem cell lines that contain targeted disruptions of the endogenous heavy and light chain loci. The transgenic organisms can synthesize human antibodies specific for human antigens, and the organisms can be used to produce human antibody-secreting hybridomas. Methods for obtaining human antibodies from transgenic organisms, such as mice, are described by Green et al., *Nature Genet.* 7:13 (1994); Lonberg et al., *Nature* 368:856 (1994); and Taylor et al., *Int. Immunol.* 6:579 (1994).

For human applications, animal-derived antibodies can be genetically manipulated or engineered to reduce their immunogenicity. For example, several chimeric or CDR-grafted humanized antibodies have been evaluated in clinical trials. See, e.g., Gavilondo, J. V., et al., *The Immunologist* 8:58-65 (2000); Glennie, M. J., and Johnson, W. M., *Immunology Today,* 21:403-10 (2000). Alternatively, human antibodies can be produced from human peripheral donor lymphocytes or generated from immunized transgenic mice known as xenomice or translocus mice, which express human immunoglobulin genes instead of the constitutive mouse genes. See, e.g., Jakobovits, A., *Advanced Drug Delivery Reviews* 31:33-42 (1998); Nicholson, I. C., et al., *Journal of Immunology,* 163:6898-6906 (1999); Gallo, M. L., et al., *European Journal of Immunology* 30:534-540 (2000).

Another approach for producing human antibodies is based on the reconstitution of irradiated and scid bone marrow radioprotected mice with human peripheral blood mononuclear cells. Such mice, called trimera mice, can be immunized and used as a source of specific human plasma cells to produce antibodies. See, e.g., Reisner, Y., and Dagan, S., *Trends in Biotechnology* 16:242-46 (1998); Eren, R., et al., *Hepatology* 32:588-596 (2000).

Antibodies also can be derived from human antibody fragments isolated from a combinatorial immunoglobulin library. See, for example, Barbas et al., in: *Methods: A Companion to Methods in Enzymology*, Vol. 2, page 119 (1991); Winter et al., *Ann. Rev. Immunol.* 12:433 (1994). Cloning and expression vectors useful for producing a human immunoglobulin phage library can be obtained, for example, from Stratagene Cloning Systems (La Jolla, Calif.).

In addition to production by hybridomas, antibodies can be produced by methods based on recombinant DNA technologies, such as phage display of combinatorial libraries or genetic engineering. See, e.g., Little, et al., *Phage Display: A Laboratory Manual*, Barbas, C. F. (Ed.), Cold Spring Harbor Laboratory Press, 2001.

An antibody can be labeled for direct detection, such as by methods described in Harlow and Lane (1998). Suitable labels include, but are not limited to, an enzyme, a radiolabel, a fluorescent label, a colorimetric label, a luminescent label, or biotin, and can be chosen based on the method of detection available to the user or other consideration.

A monoclonal antibody can be conjugated with a desired agent, such as a therapeutic agent or metal chelate. These agents can be conjugated chemically, using a chemical reaction that is dependent upon the functional groups present on the agent to be conjugated, produced by photocrosslinking, or generated using other techniques. See, e.g., Best, U.S. Pat. No. 5,082,928 and references contained therein.

The antibodies disclosed herein include intact molecules, and fragments thereof, capable of binding the epitopic determinant of their cognate antigens. Antibody fragments can be produced by a variety of methods, such as by the targeted proteolysis methods described in Harlow and Lane (1998), or recombinant DNA techniques. See, e.g., Little, M., et al., *Immunology Today* 21:364-370 (2000). Alternatively, the nucleic acid sequences encoding the heavy and light chains of an antibody can be cloned using universal but immunoglobulin-specific primers, sequenced, and produced in vitro using a variety of expression systems. See, e.g., Ladiges, W., and Osman, G. E., in: *Basic Methods in Antibody Production and Characterization*, Howard, G. C., and Bethell, D. R. (Eds.), CRC Press, Boca Raton, 2001, pp. 169-91.

Antibody fragments can be prepared by proteolytic hydrolysis of the antibody or by in vivo expression of DNA encoding the fragment. Antibody fragments can be obtained by pepsin or papain digestion of whole antibodies by various methods, such as the methods described in Goldenberg, U.S. Pat. Nos. 4,036,945 and 4,331,647, and references contained therein. See also Nisonhoff et al., *Arch. Biochem. Biophys.* 89:230 (1960); Porter, *Biochem. J.* 73:119 (1959); Edelman et al., *Methods in Enzymology*, Vol. 1, page 422, Academic Press (1967); and Coligan et al. (1992) at sections 2.8.1-2.8.10 and 2.10.1-2.10.4.

Another form of an antibody fragment is a peptide coding for a single complementarity-determining region (CDR). CDR peptides, also known as "minimal recognition units," can be obtained by constructing nucleic acid sequences encoding the CDR of an antibody of interest. Such nucleic acid sequences are prepared, for example, by using the polymerase chain reaction (PCR) to synthesize the variable region from RNA of antibody-producing cells. See, for example, Larrick et al., *Methods: a Companion to Methods in Enzymology*, Vol. 2, page 106 (1991).

Other methods of cleaving antibodies, such as separation of heavy chains to form monovalent light-heavy chain fragments, further cleavage of fragments, or other enzymatic, chemical, or genetic techniques also can be used, so long as the fragments bind to the antigen that is recognized by the intact antibody.

It is also possible to use anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

Methods of Using Antibodies

Antibodies disclosed herein can be used as experimental research tools, or for diagnostic, prophylactic, or therapeutic purposes in a clinical setting. Additionally, these antibodies can be used to detect and/or monitor fungi in plants, animals, or the environment according to their individual cross-reactivity profiles, as summarized in Table 2 below. For example, Mab 9B4 can be used for species-specific detection of *Stachybotrys chartarum* spores.

In some embodiments, an antibody is used to detect the presence of or exposure to a fungus within an original or processed sample obtained from the environment, a plant, or an animal. Samples obtained from the environment include soil, water, dust, bulk samples (e.g., building material or furniture), air, and other reservoir samples, such as animal feed, collected in an indoor or outdoor environment. For example, air samples may be collected in a ventilation duct of a building. Samples obtained from a plant or animal may include a cell, tissue, biopsy, extracted gall, secretion, or fluid from the subject. Regarding animal subjects, the sample may be obtained from a bodily fluid (e.g., urine, lymph, blood, serum, plasma, cerebrospinal fluid, saliva, and swipe or smear samples from mucosal surfaces) or gastric contents (i.e., the contents of the gastrointestinal system, including stomach contents, gastrointestinal biopsy, and feces). In particular embodiments, the sample is obtained from a lung of an animal, such as by biopsying lung tissue, or collecting a bronchial, bonchioalveolar, nasal, or sputum sample.

The sample in its entirety can be taken solely from the subject, such as by probing or scraping, or can be collected through the addition of some other substance or compound. For example, a sample can simply be blood or urine collected from a subject animal and aliquotted for contacting with the monoclonal antibody. As an alternative example, a sample can be obtained from a plant, animal, or some environmental surface by surface washings with sterile water, a dedicated extraction buffer, or other suitable fluid.

A sample can be analyzed directly, extracted before analysis, or expanded in volume by the addition of a suitable solvent. For example, a sample of fungal spores can be collected using a screen or trap placed in a ventilation duct of a building; the spores collected from the airflow through the duct can be fragmented and suspended in solution. If the type or volume of sample obtained is not sufficient for screening with the antibody, the sample can be expanded by the addition of a suitable organic or inorganic solvent, or can be expanded by culturing in a growth medium suitable for culturing fungi suspected of being in the sample.

The sample is contacted with an amount of monoclonal antibody, and the samples are screened to detect a monoclonal antibody complexing with an antigen, such as detecting the binding reaction between the antibody and antigen. Detection of an antibody-antigen complex or binding reaction indicates that the sample was exposed to or contacted by a fungus having an antigen to the antibody. In some instances, the fungus (spores, mycelium, or both) is still present in the sample. In other instances, the fungus has degraded, disappeared from, or been eliminated from the sample, leaving behind antigenic components.

For example, labeled 9B4 monoclonal antibodies can be used to detect antigen of *Stachybotrys chartarum* spores, thus indicating that the sample was exposed to *Stachybotrys chartarum* spores. In some embodiments, the antibody is labeled with an environmentally sensitive label, such as a fluorescent label, so that its signal changes upon binding to antigen. In other embodiments, antigen in the sample is immobilized on a surface prior to introduction of the labeled antibody, and the amount of the signal, corresponding to the amount of bound labeled antibody, correlates to the amount of antigen in the sample. In still other embodiments, antigen is captured by immobilized unlabeled first antibody, after which a labeled second antibody is introduced to bind to the captured antigen and produce a signal in proportion to the amount of captured antigen.

If the sample was obtained from the environment, such as an air sample obtained from the ventilation duct of a building, then the environment can be searched for the presence of *Stachybotrys chartarum*. For animal subjects, particularly people and domesticated animals, a determination of *Stachybotrys chartarum* exposure can aid in diagnosing disease and developing treatment regimens.

In addition to using an antibody to detect an antigen, the antibody can be used to isolate its corresponding antigen, and the antigen can then be used to detect the presence of that antibody or other antibodies to that antigen. For example, an antibody can be used to affinity purify its cognate antigen, which can then be used in competition assays to quantify homologous antigen in a sample obtained from a plant, animal, or the environment.

In such embodiments, a monoclonal or polyclonal antibody is isolated and purified and used in an immunoprecipitation procedure to isolate the corresponding antigen from a mixture of soluble molecules, such as a suspension of lysed cells. Exemplary immunoprecipitation procedures can be found in Harlow and Lane (1998), chapter 7. Once the antigen has been isolated, it can be analyzed by determining characteristics such as molecular weight, sequence, and three-dimensional structure. Such characterization is not necessary for subsequent uses of the antigen, however. Once isolated, the antigen is used to screen a sample to detect the presence of a cognate antibody. In some embodiments, the antigen is labeled, and the labeled antigen is used to detect cognate antibody in the same way that labeled antibody is used to detect antigen (described above). In other embodiments, the antigen is immobilized, and antibody is captured and then detected, for example, by ELISA.

Purified antigen can be used to identify the presence of a corresponding antibody in an animal subject, thus establishing that the animal subject was exposed to a fungal-antigen recognized by the antibody. For example, monoclonal antibody 9B4 can be used to isolate and immunoprecipitate its corresponding antigen (see Example 4), and this antigen can be labeled and used in a solid-phase or competition assay to screen a blood sample obtained from a human patient for the presence of antibody to that antigen, the presence of antibody indicating that the person was exposed to *Stachybotrys chartarum*.

Additionally, antibodies also can be utilized to screen phage displayed or synthetic expression libraries for peptides or mimotopes that may be used as functional single-epitope antigens. Such mimotopes can be considered species-specific, if the template antibody used for screening is species-specific. Thus, by reducing antigens to the size of epitopic peptides, potential ambiguities due to other epitopes expressed by the full length parent molecule can be avoided. For example, fungi have been found to share epitopic determinants and to cross-react widely. Thus, the production of mimotopes for Mab 9B4 can allow the development of definitive exposure measurement techniques for animal subjects. The antibodies also can be used in quality assurance, standardization, and characterization of fungal extracts to be used in clinical practice or research.

The disclosed antibodies can be used in a variety of immunometric assays, including radiolabeled, enzyme, fluorescence, precipitation, agglutination, coagulation, Western blot, grid blot, tissue blot, dot blot, chemiluminescence, light-scattering, electrochemical, dip-stick, or biosensor assays. See, e.g., *Principles aid Practice of Immunoassays*, Price, C. P. and Newman, D. J. (Eds.), Stockton Press, 1997; *The Immunoassay Handbook*, $2^{nd}$ Edition, Wild, D. (Ed.), Nature Publishing Group, London, 2001. In general, an antibody can be used as a labeled primary reagent in a direct assay or as an unlabeled reagent to be detected by a secondary developing antibody conjugate, such as labeled anti-mouse antibody, in an indirect assay. Additionally, an antibody can be used in a competition assay to detect an antigen or antibody in a sample. For example, antigen in a sample extract can be captured by an unlabeled antibody immobilized on the surface of an ELISA well and then detected by a labeled antibody of the same or different kind and/or specificity. Alternatively, the sample can be suspended in a buffer and mixed directly with an antibody, thus allowing the antibody to form an immune complex with its antigen. The reduction of free antibody due to complex formation can then be determined in a second step, based on solid-phase ELISA with purified antigen, by comparing the relative reactivity of free residual antibody left over after sample incubation (sample reactivity) to that of the same antibody when not mixed with the sample (reference reactivity). The ratio of sample to reference antibody reactivity will be inversely proportional to the amount of antigen in the sample.

In other embodiments, an antibody is used for the detection of fungal propagules on collection surfaces, such as transparent adhesive tapes or air filters, using fluorescent microscopy, a halogen assay, or some other detection method. See, e.g., O'Meara, T., and Tovey, E., *Clinical Reviews in Allergy and Immunology* 18:341-95 (2000). For example, fluorescently labeled Mab 9B4 can be used to detect spores of *Stachybotrys chartarum*. In a halogen assay, air particles are collected via an adhesive tape, and antigens are transferred by elution to a laminated protein-binding membrane. Particle-characteristic binding patterns, such as halos or spots, are formed on the membrane, and the patterns are visualized for counting by antibody-mediated particle staining using insoluble enzyme substrates.

Antibodies also can be used to test the effectiveness of an agent in complexing with a fungal antigen. In some embodiments, a monoclonal antibody is mixed with its antigen and an agent. The antigen can be borne on a fungus or a portion of the fungus, or purified apart from the fungus. The mixing of the antibody, antigen, and agent can be accomplished in vitro or in vivo. An agent that complexes with the same antigen as the antibody will inhibit the antibody-antigen binding reaction. Therefore, a decrease in antibody-antigen binding in the presence of the agent compared to some reference standard (e.g., background fluorescence) or control (e.g., antibody-antigen binding in the absence of the agent) indicates that the agent may interact with the antigen. One exemplary method of assessing antibody-antigen binding is to analyze the kinetics of the binding reaction and determine a rate of binding. Other exemplary methods include determining the total amount of antibody-antigen binding at equilibrium.

In other embodiments, an antibody is used in histochemistry or image analysis to visualize, identify, localize or quantify specific molecules, such as being used in proteomics to describe protein expression patterns for signal transduction or in metabolic pathways. In clinical applications, an antibody may be used for environmental or patient monitoring in allergy or toxicology applications, for immune suppression and tolerance induction in autoimmunity and transplantation, or for the treatment of infections or tumors. For example, a Mab conjugated to a toxin, prodrug, or radioisotope can be used in antibody-guided therapy for disease or infection. Bamias, A., and Epenetos, A. A., in: *Monoclonal Antibodies—Production, Engineering and Clinical Applications*, Ritter, M. A. and Ladyman, H. M. (Eds.), Cambridge University Press, Cambridge, 1995, pp. 222-46. As another example, a Mab can be used as a surrogate antigen in anti-idiotype therapy, or an antibody can be genetically engineered as an antigenized antibody to express an antigen in a complementarity-determining region. See, e.g., Polonelli, L., et al., in: *The Antibodies— Volume 4*, Zanetti, M. and Capra, J. D. (Eds.), Harwood Academic Press, Amsterdam, The Netherlands, 1997, pp. 143-66; Bona, C. A., *Nature Medicine* 4:705-706 (1998); and Vogel, M., et al., *Journal of Molecular Biology* 298: 729-735 (2000).

An antibody also can be used to direct an agent—such as an antibiotic, therapeutic agent, or metal chelate—to a fungus. In some embodiments, an antibody is conjugated with the agent and the conjugated agent is then able to target a particular fungus or several different fungi, depending on which antibody is used. The antibody portion of such a conjugate may complex with antigens found on a fungus and, thus, bring the agent into effective proximity of the fungus. For example, a fungi static agent effective against *Stachybotrys chartarum* conjugated with the 9B4 monoclonal antibody would selectively target *Stachybotrys chartarum* spores. Moreover, if the antigen has been secreted from the fungus, or if the fungus has disintegrated, the antibody-agent complex can bind the antigen and prevent that antigen from interacting with other molecules.

In particular embodiments, an antibody-agent conjugate, such as a Mab-fungistatic or Mab-fungitoxic compound, is introduced into a particular locus of the environment. For example, conjugates of Mab 9B4 can be applied to particular sites within a building known or suspected to be contaminated by *Stachybotrys chartarum*.

In other embodiments, an antibody-agent conjugate, such as a Mab-fungistatic or Mab-fungitoxic compound, is introduced into a subject animal or plant for diagnostic, prophylactic, therapeutic, or other purposes. For example, Mab 3B2 conjugates can be used to target therapeutic agents or prodrugs to fungal spores or mycelia in a subject known or suspected to be exposed to any of *Aureobasidium pullulans, Cladosporium cladosporioides, Cladosporium herbarum, Cladosporium sphaerospermum, Memnoniella echinata, Myrothecium verrucaria, Stachybotrys albipes, Stachybotrys bisbyi, Stachybotrys chartarum, Stachybotrys cylindrospora, Stachybotrys microspora, Stachybotrys nephrospora*, or *Stachybotrys subsimplex*.

Some embodiments include a kit or article of manufacture that includes an antibody. In these embodiments, an antibody is stored within a container capable of storing the antibody for its shelf life. The container can be made of any suitable material such as plastic or other polymer, glass, metal, or the like. Printed instructions and/or a printed label indicating a method of use for the antibody, such as instructions describing how the antibody can be used to detect fungi, can be associated with the container. The instructions and/or label may provide information regarding the use of the antibody for any of the purposes in accordance with the methods set forth herein and can be associated with the container by being adhered to the container or accompanying the container in a package. Additionally, the container can include a feature or device for using the antibody. In certain embodiments, the article of manufacture includes, packaged together, a vessel containing the antibody and instructions for use of the antibody for detecting a fungus.

EXAMPLES

The following examples are provided to illustrate particular features of certain embodiments, but the scope of the claims should not be limited to those features exemplified.

Example 1

Preparation of a Parent Hybridoma

Spores of *Stachybotrys chartarum* were harvested from sporulating, air-dried 7-day old culture plates containing 5 ml of malt extract broth agar. Two isolates of *Stachybotrys chartarum*, one toxigenic and one non-toxigenic, were used as an antigen mixture. Spores were collected from sporulating cultures with 1 g of glass beads (0.45-0.5 mm, B. Braun Biotech International, Melsungen, Germany), which were gently shaken across fungal colonies. This allowed ample spores to attach to the beads and also allowed easy recovery of the spores for ELISA analysis by simply shaking the beads in a 50 ml tube containing carbonate coating buffer (CCB).

Three, 12-week old female BALB/c mice, obtained from the animal facility of the National Institute for Occupational Safety and Health, were immunized intraperitoneally approximately every two weeks for several months. For immunogen preparation, harvested spores were suspended in 10 mM phosphate buffered saline (PBS, Sigma, St. Louis, Mo.), counted, and washed twice by centrifugation at 15 g for 5 min in PBS supplemented with 0.05% Tween 20 (PBST). The final pellet was re-suspended in PBS, and 1 ml aliquots of the spore suspension were supplemented with 1 g of glass beads (0.45-0.5 mm, B. Braun Biotech International, Melsungen, Germany). Spores were then mechanically homogenized using a bead beater for three, 2 min intervals, while being kept on ice for 2 min between intervals. The aliquots were combined, and particulate cell debris was collected in PBS after two washes by centrifugation at 15 g for 10 min. Mice were immunized with the particulate fraction at concentrations equivalent to the spore numbers shown in Table 1.

TABLE 1

Immunization of mice

| Treatment | Immunized Spores per Mouse |
|---|---|
| 1st immunization | $1 \times 10^6$ |
| 2nd immunization | $0.5 \times 10^6$ |
| 3rd immunization | $2.5 \times 10^6$ |
| 4th immunization | $5 \times 10^6$ |
| 5th immunization | $1.5 \times 10^6$ |
| 6th immunization | $2 \times 10^6$ - Mouse 1 |
|  | $1 \times 10^6$ - Mice 2 and 3 |
| 7th immunization | $2 \times 10^6$ - Mouse 2 |
|  | $1 \times 10^7$ - Mouse 3 |

Hyperimmune mice were sacrificed and single cell suspensions were prepared from aseptically removed spleens. Ladyman, H. M., and Ritter, M. A., in: *Monoclonal Antibodies—Production, Engineering and Clinical Application*, Ritter, M. A. and Ladyman, H. M. (Eds.), Cambridge University Press, Cambridge, UK, 1995, pp. 429-66. Splenocytes containing antigen-reactive plasma cells were fused with SP2/0-AG14 myeloma cells (Cat# CRL-1581, ATCC, Manassas, Va.) using polyethylene glycol 1500 (Boehringer Mannheim, Germany) as fusogen. Yokoyama, W. M., *Cur-* rent *Protocols in Immunology*, Supplement 13:2.5.1 to 2.5.17 (1991). The fusion product of each individual fusion was suspended in 100 ml selective medium (Dulbecco's Modified Eagle Medium (DMEM), Life Technologies, Rockville, Md.) supplemented with 1 mM Pyruvate (Life Technologies, Rockville, Md.), 100 units/ml penicillin, 100 μg/ml streptomycin, 0.292 mg/ml L-glutamine (Life Technologies, Rockville, Md.), 10% FCS (HyClone, Logan, Utah), 100 μM sodium hypoxanthine (Life Technologies, Rockville, Md.)), 0.57 μM azaserine (Sigma, St. Louis, Mo.) and 100 units/ml IL-6 (Life Technologies, Rockville, Md.). Cells were seeded at 100 μl/well in 96-well tissue culture plates for incubation at 37° C. in 10% $CO_2$ in air. Cells were maintained in DMEM without azaserine, and culture supernatants were screened for reactivity to spores of *Stachybotrys chartarum*. Clones of positive wells were cloned twice by limiting dilution to ensure monoclonality and bulk grown in tissue culture plates to provide culture supernatant for Mab characterization. Stable clones were cryoprotectively stored in liquid nitrogen. Fusion 1 resulted in the production of Mabs 3B2 (IgM) and 10A5 (IgM), fusion 2 generated Mabs 1D4 (IgM) and 9B4 ($IgG_1$), and fusion 3 produced Mabs 9F9 (IgM) and 4E12 (IgM).

Example 2

Development of a Detection ELISA and Characterization of Monoclonal Antibodies

Mabs produced in Example 1 were tested for cross-reactivity by ELISA against mycelial extracts of 12 isolates of *S. chartarum* (FIG. 2) and 29 related and unrelated fungi commonly found in indoor environments (FIG. 4). Mabs also were tested against spores of 14 isolates of *S. chartarum* and eight other *Stachybotrys* species (FIG. 1) and 43 other fungi commonly found in indoor and outdoor environments (FIG. 3). ELISA plate wells were coated with mycelial extracts at 10 μg/ml protein or with spores at concentrations shown with the species code abbreviations.

Spores were harvested as described in Example 1, and mycelial extracts were prepared in liquid culture using spores as seeding inoculum. Sporulating slant cultures were washed with 2 ml of PBS, which was then transferred to flasks containing 200 ml of Malt Extract Broth. Flasks were incubated at room temperature (RT) and rotated at 200 rpm. Mycelium was harvested after 10-11 days using a fine nylon mesh, and aliquots were stored at −20° C. until further processing. For extraction, mycelium was washed in 50 ml carbonate/bicarbonate coating buffer (CCB: 60 mM $Na_2CO_3$, 140 mM $NaHCO_3$, pH 9.6), shaken briefly, and pelleted at 15 g for 10 min before being sonicated in 25 ml of CCB while kept on ice for 2 min. The sonicate was cleared by centrifugation at 15 g for 10 min before being centrifuged at 40,000 g for 20 min. The supernatant was stored at −20° C. until used for cross-reactivity tests.

For ELISA analysis, wells of PolySorp ELISA plates (Nalge Nunc, Naperville, Ill.) were coated with a 100 μl suspension of spores or mycelium and incubated in a moist chamber at RT. After overnight incubation, wells were rinsed with three 10 min PBST-washes before unoccupied binding sites in the wells were blocked with 200 μl of PBST containing 1% nonfat dry milk powder (Kroger, Cincinnati, Ohio) for 1 h at RT. Plates were washed and incubated for 1 h at 37° C. with 100 μl of Mab culture supernatant (CSN) diluted 5 times with PBST. After washing, bound Mab was detected with a 1/5000 PBST-diluted goat anti-mouse antibody conjugated to biotin (JacksonImmuno Research, West Grove, Pa.) by incubation at 37° C. for 1 hour. After washing, bound biotin was labeled with a 1/5000 dilution of alkaline phosphatase-conjugated streptavidin (JacksonImmuno Research, West Grove, Pa.) in PBST by incubation for 1 hour at 37° C. Excess reagent was washed out, and the optical density (OD) at 405 nm was determined using an ELISA reader (Bio-Tek Instruments, Winooski, Vt.) after incubating the substrate p-nitrophenyl phosphate (Sigma, St. Louis, Mo.) at 0.5 mg/ml in 100 mM diethanol-amine buffer for 30 min at 100 μl/well. Negative controls were incubated with plain CSN instead of Mab-containing CSN and processed in parallel. Optical densities of 0.05 above the negative controls after 30 min of substrate incubation time (SIT) were considered to be positive results:

As shown in FIGS. 1-4 and summarized in Table 2, all Mabs—except Mab 9B4—were found to cross-react with spores and mycelia of multiple fungal species.

TABLE 2

Summary of species profiles of disclosed monoclonal antibodies

| Mab | Positive reactivity to spores | Positive reactivity to mycelium |
|---|---|---|
| 1D4 | Fox, Mec, Mve, Sal, Sbi, Sch, Scy, Sec, Smi, Sne, Ssu, Tha, Ska | Mec, Sch, Tha |
| 3B2 | Apu, Ccl, Che, Csp, Mec, Mve, Sal, Sbi, Sch, Scy, Sec, Smi, Sne, Ssu, Ska | Ccl, Mec, Mve, Sch |
| 4E12 | Apu, Ccl, Che, Csp, Mec, Mve, Sal, Sbi, Sch, Scy, Sec, Smi, Sne, Ssu, Ska | Ccl, Mec, Sch |
| 9B4 | Sch | None |
| 9F9 | Aca, Ani, Asy, Apu, Ccl, Che, Csp, Mec, Mve, Rst, Sal, Sbi, Sch, Scy, Sec, Smi, Sne, Ssu, Ska, Uch | Ccl, Mec, Sch |
| 10A5 | Apu, Ccl, Che, Csp, Mec, Mve, Sal, Sbi, Sch, Scy, Sec, Smi, Sne, Ssu, Ska | Ccl, Mec, Mve, Sch |

Thus, Mab 9B4 can be used to species-specifically detect the presence of *Stachybotrys chartarum* spores in samples. The other five Mabs, while reacting with all tested *Stachybotrys* and *Memnoniella* species, show characteristic reaction patterns with other fungi and can be classified into 3 distinct groups. In group 1, Mabs 9F9 and 4E12 react with spores and mycelium of all *Cladosporium* species tested, but react only with spores, and not mycelium, of *Aureobasidium* and *Myrothecium*. Both Mabs also show some minor reactivity to spores of some other species. In group 2, Mabs 3B2 and 10A5 show similar reactivity patterns when compared to group 1, but in addition to spores, these Mabs also recognize mycelium of *Myrothecium*. This reaction pattern and the spore specificity of Mab 9B4 indicate that fungal spores and mycelium express unique epitopes, and that the above immunization protocol with spores can be used as a method to generate spore-specific Mabs. Group 2 Mabs also are more sensitive than group 1 Mabs. Since both Mabs in each group show very similar reactivity patterns to each other, and due to the fact that in each case they were derived from a single mouse, these Mabs might well represent clones of the same plasma cell activated during the immune response in each of these mice to *Stachybotrys chartarum*. In group 3, Mab 1D4 reacts with spores and mycelium of all *Stachybotrys* and *Memnoniella* species and also reacts with spores and mycelium of *Trichoderma*, but does not react with *Cladosporium* species. Mab 1D4 also confirms antigenic differences between spores and mycelium by reacting with spores, but not mycelium, of *Myrothecium*.

Figure 1:
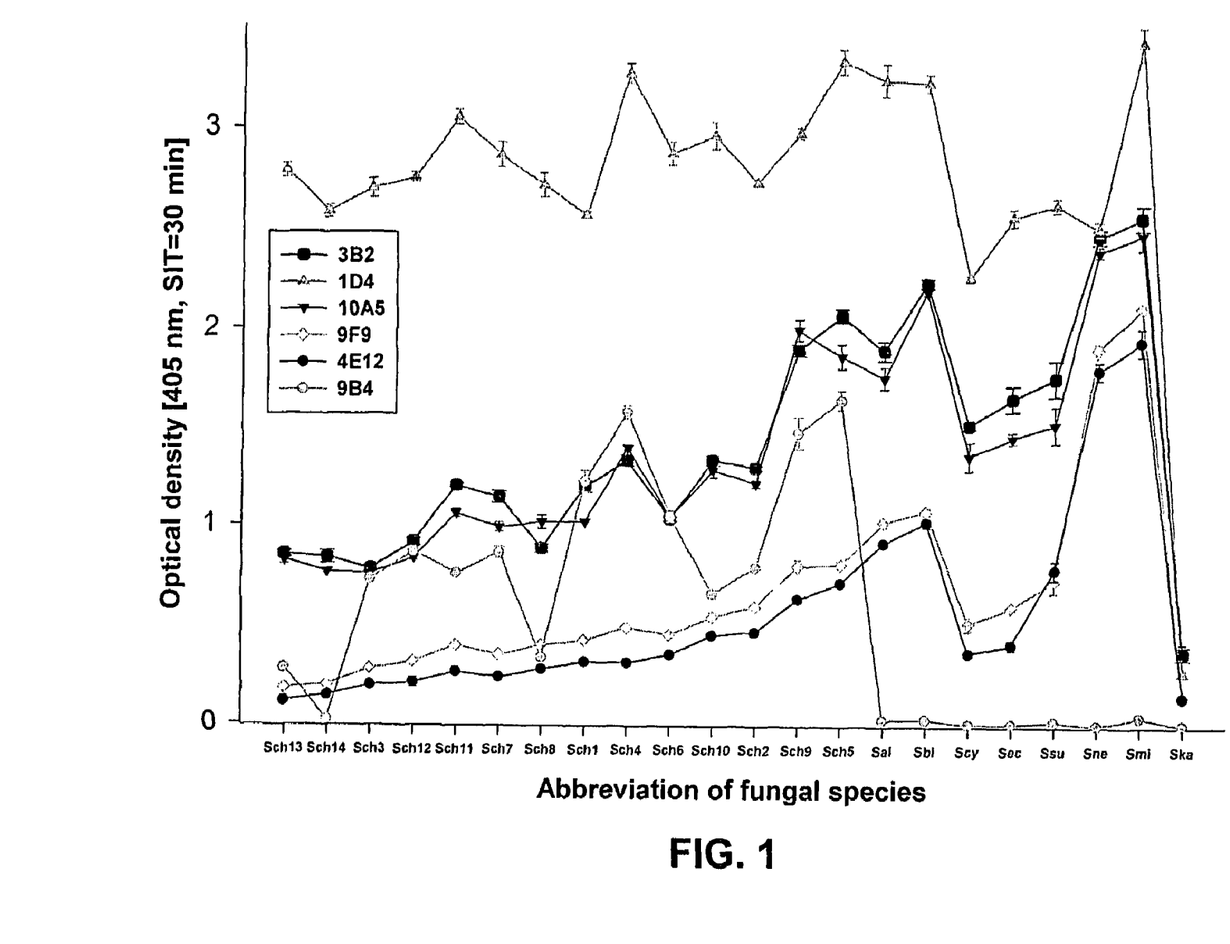
FIG. 1 is a graph illustrating the cross-reactivity of several monoclonal antibodies (Mabs) with spores of different *Stachybotrys* species and different *Stachybotrys chartarum* isolates.
Figure 2:
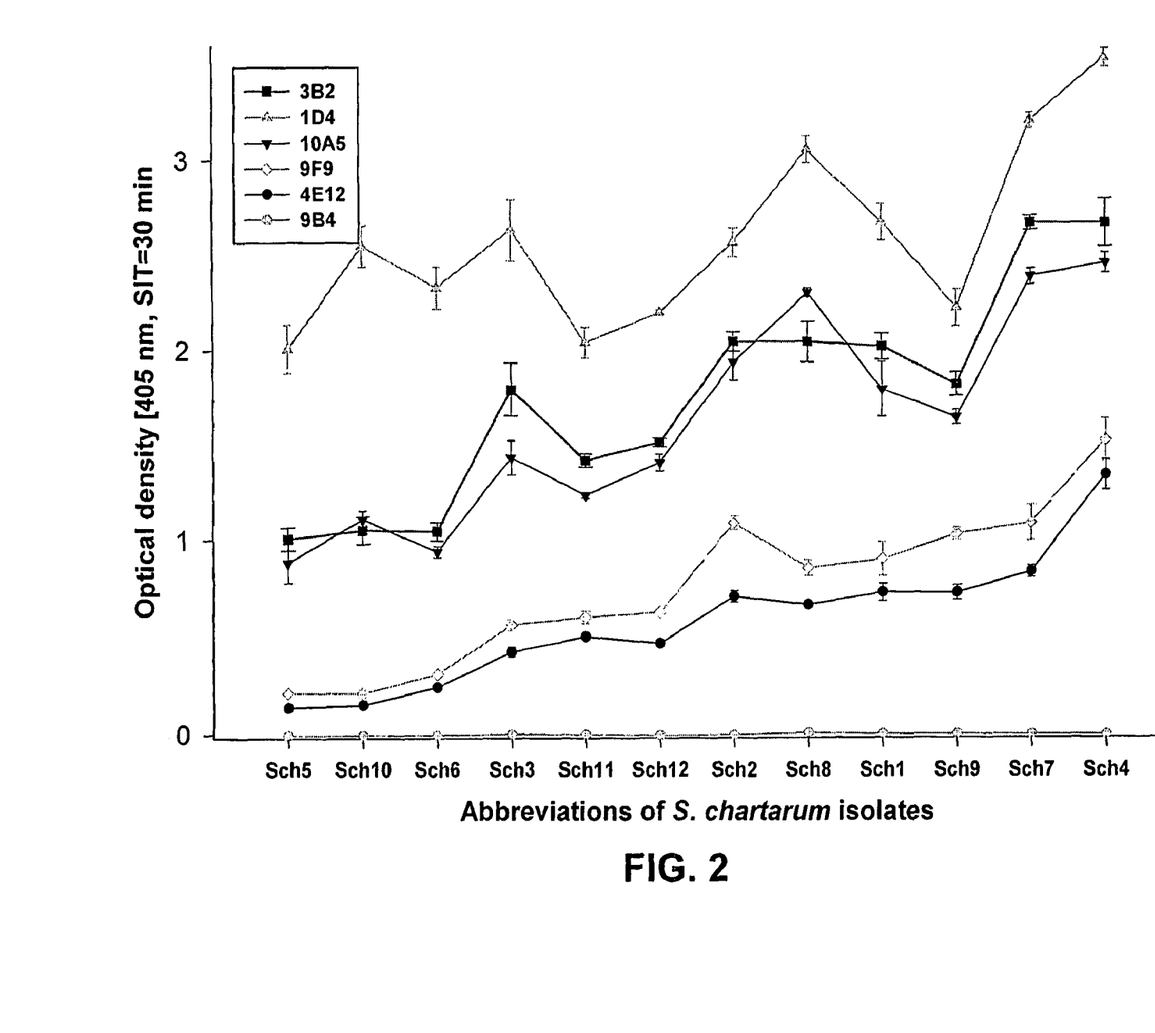
FIG. 2 is a graph illustrating monoclonal antibody (Mab) reactivity to mycelium of different *Stachybotrys chartarum* isolates.
Figure 3:
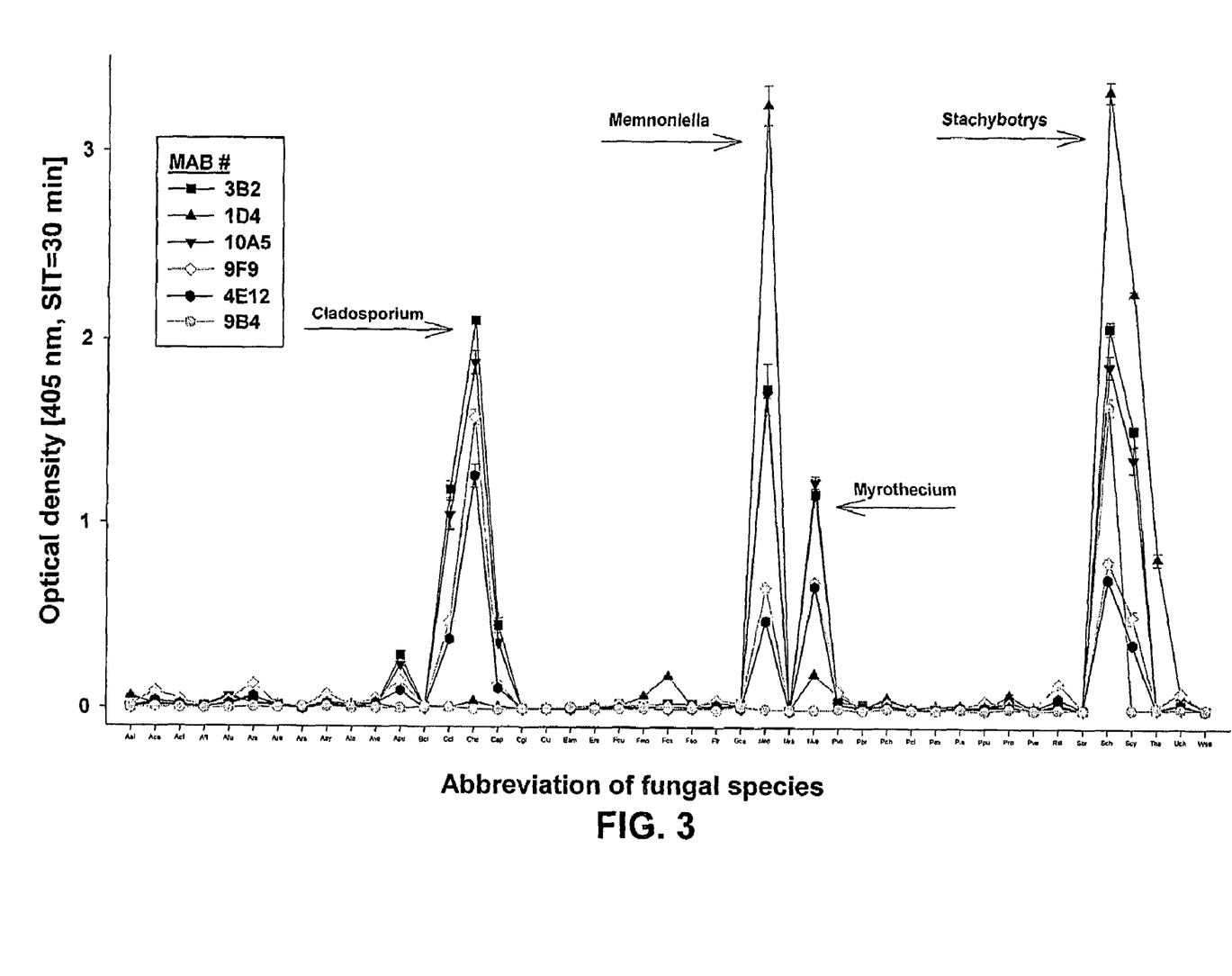
FIG. 3 is a graph illustrating the cross-reactivity of several different Mabs against spores of fungal species commonly found in indoor environments.
Figure 4:
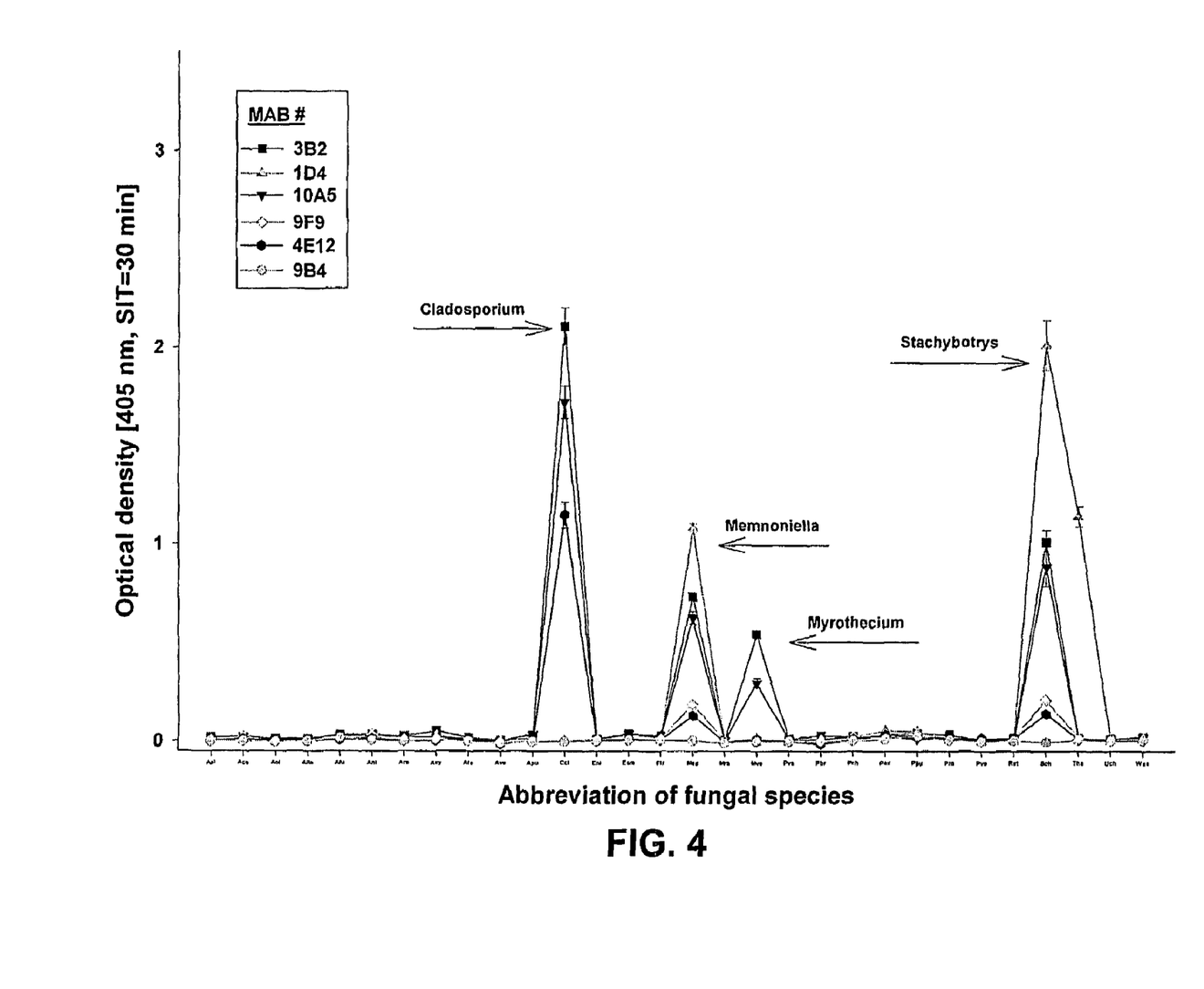
FIG. 4 is another graph illustrating the cross-reactivity of several different Mabs against mycelium of several fungal species commonly found in indoor environments.

FIG. 2 not only shows that Mab 9B4 does not react with mycelium of *Stachybotrys chartarum*, but also shows that the reactivity of all other Mabs varies according to, different isolates of the fungus. Since the amount of antigen was standardized to 10 µg/ml for all twelve isolates, the differential Mab reactivity indicates that the antigenic composition of individual isolates varies either due to absolute or relative numbers of antibody-reactive epitopes per unit biomass in the original mycelial extract.

Figure 5:
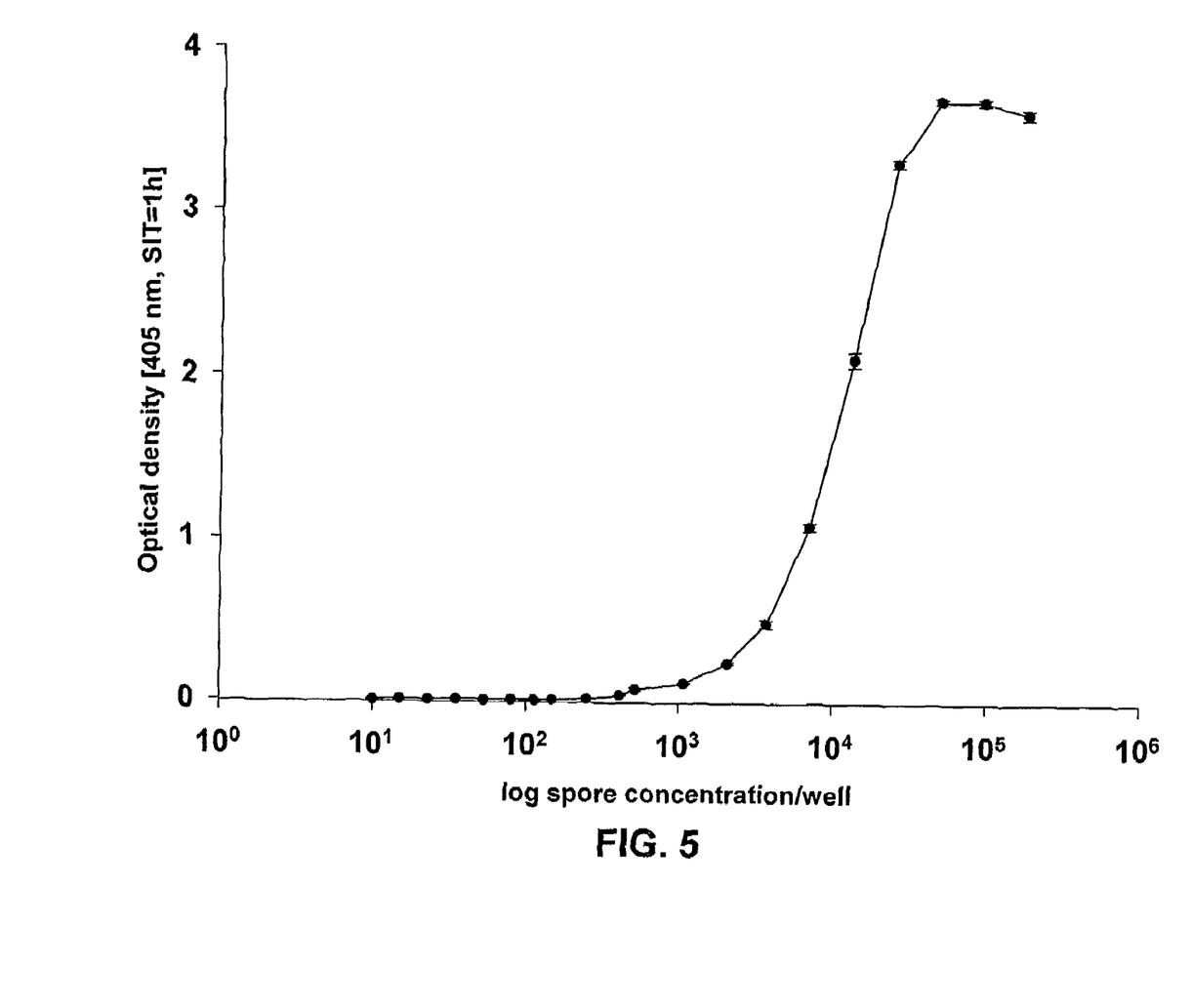
FIG. 5 is a graph illustrating the sensitivity of Mab 9B4 against different *Stachybotrys chartarum* spores using enzyme-linked immunosorbent assay (ELISA).

FIG. 5 shows the sensitivity of Mab 9B4 against spores of *Stachybotrys chartarum* in ELISA. It can be seen that the lower and upper values of the linear range of detection are 2000 and 40,000 spores/well, respectively. This degree of assay sensitivity is significantly better than that reported for Mabs produced against fungal allergens of *Alternaria alternata*, in which case $10^5$ to $10^6$ spores were required for the detection of the fungus. Vailes, L., et al., *Journal of Allergy and Clinical Immunology* 107:641-646 (2001). However, it is less than the reported 5 to 400 germinating spores detectable by Mabs against *Alternaria brassicae*, which were also produced against whole spores and spore germlings rather than individual molecules or allergens. Schmechel, D., et al., *Food and Agricultural Immunology* 9:219-32 (1997). These results indicate that whole spores, rather than isolated molecules, may be the antigen of choice to produce specific and highly sensitive Mabs against fungi.

Figure 6:
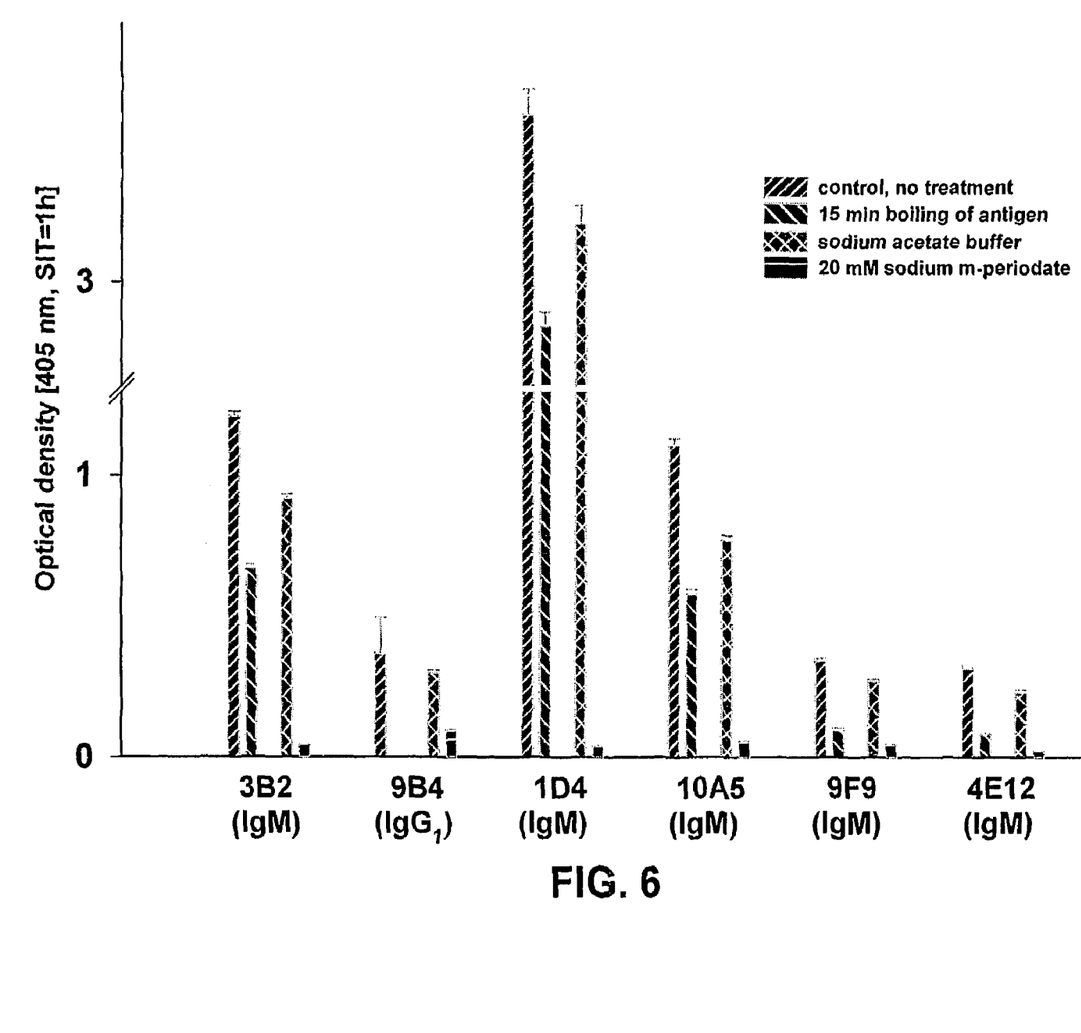
FIG. 6 is a graph illustrating the effect on Mab binding after boiling and periodate treatment of the antigen.

FIG. 6 illustrates the effects of antigen boiling and periodate oxidization for 4 hours at RT with 20 mM sodium m-periodate in 0.1 M sodium acetate buffer, pH 4, on ELISA reactivity of all Mabs. It can be seen that boiling completely inhibits the reactivity of Mab 9B4 ($IgG_1$), while some binding activity remained after periodate treatment. These results indicate that the epitope of Mab 9B4 is a protein or a glycoprotein. On the other hand, while boiling reduced the reactivity of all other Mabs, periodate oxidation almost completely inhibited their binding. These results, and the fact that these Mabs are all of the IgM isotype, indicates that their epitopes are based on carbohydrates, not proteins.

Example 3

Purification of Mab 9B4

Mab 9B4 will be purified and concentrated from culture supernatants of tissue culture plates or flasks and from supernatants harvested from the extra capillary space of a CELLMAX artificial capillary cell culture system (Spectrum Laboratories, Rancho Dominguez, Calif.). For tissue culture plates, cells are allowed to reach confluence, and when 70-80% of the cells are dead, supernatant is harvested by centrifugation at 1000 g for 5 min and passed sequentially through a 0.45 µm and a 0.22 µm filter (Whatman, Clifton, N.J.), respectively. For the CELLMAX system, hybridomas are grown at cell densities of $1-10 \times 10^8$ per cartridge and harvested periodically. Supernatants are combined, filtered as above, and used for Mab purification.

Mabs are purified using protein G and protein L (Sigma, St. Louis, Mo.) affinity chromatography. Protein G is used to deplete bovine immunoglobulins from fetal calf serum prior to its use for tissue culture of hybridomas, thus producing Mab culture supernatants free of bovine IgG. Darby, C. R., et al., *Journal of Immunological Methods* 159:125-29 (1993). Protein L is used to purify and concentrate Mab 9B4 according to the protocols of Harkins (*Basic Methods in Antibody Production and Characterization*, Howard, G. C., and Bethell, D. R. (Eds.), CRC Press, Boca Raton, Fla., pp. 141-168) and Heelan (*Methods in Molecular Medicine* 40:281-88 (2000)).

Example 4

Purification of *Stachybotrys chartarum*-Specific Antigen Using Mab 9B4

Specific antigen will be purified using Mab 9B4-mediated affinity chromatography. Mab 9B4 is covalently linked to Protein G beads (Sigma, St. Louis, Mo.) using a cross-linking, bi-functional coupling reagent, such as dimethyl pimelimidate, and established protocols. Harlow, E., and Lane, D. (Eds.), 1998. The Mab 9B4-beads are then incubated with the supernatant of sonicated spores of *Stachybotrys chartarum*, which will have been previously incubated overnight on a rocking platform. The beads are packed into a column and antigen is collected by elution.

Example 5

Detection of *Stachybotrys chartarum*-Specific Antibodies in Animal Samples

*Stachybotrys*-specific antibodies will be detected by direct ELISA or by competitive inhibition ELISA.

For direct ELISA, ELISA plates will be coated at 10 µg/ml of purified antigen and animal antibodies will be detected using the ELISA format described in Example 2, with titrated animal serum instead of Mab CSN and animal-specific biotin antibody conjugates (JacksonImmuno Research, West Grove, Pa.).

For inhibition ELISA, ELISA plates are also coated with 10 µg/ml of purified antigen and Mab 9B4 reactivity in competition with titrated animal serum is analyzed using the ELISA described in Example 2. The degree of 9B4 inhibition is proportional to the amount of specific antibodies present in the animal serum. Since the antigen was purified with the *Stachybotrys chartarum*-specific Mab 9B4, the antigen can likewise be considered to be *Stachybotrys chartarum*-specific and, in turn, establish exposure to the fungus following a positive inhibition test.

Mimotopes, isolated from constrained phage display libraries (*Phage Display: A Laboratory Manual*, Barbas, C. F. (Ed.), Cold Spring Harbor Laboratory Press, 2001; *Phage Display of Peptides and Proteins*, Kay, B. K., et al. (Eds.), Academic Press, San Diego, Calif., 1996) also will be explored in the direct and inhibition ELISA to provide epitope-specific tests.

Having illustrated and described the principles of the invention by several embodiments, it should be apparent that those embodiments can be modified in arrangement and detail without departing from the principles of the invention. Thus, the invention as claimed includes all such embodiments and variations thereof, and their equivalents, as come within the true spirit and scope of the claims stated below.

We claim:

1. An isolated 9B4 monoclonal antibody wherein the antibody binds to *Stachybotrys chartarutn*.

2. A kit for detecting the presence of *Stachybotrys chartarum*, comprising a container containing the monoclonal antibody according to claim 1.

3. The kit according to claim 2, further comprising instructional material.

4. The monoclonal antibody of claim 1, wherein the antibody is labeled.

5. A hybridoma cell line that secretes the 9B4 monoclonal antibody as set forth in claim 1 deposited on Aug. 9, 2002 with the American Type Culture Collection under accession number PTA-4582.

6. A method of detecting *Stachybotrys chartarum*, comprising:
   contacting the antibody of claim 1 with a sample; and
   detecting a complex comprising the antibody bound to an antigen from *Stachybotrys chartarum*.

7. The method according to claim 6, wherein the antibody is immobilized.

8. The method according to claim 6, wherein detecting further comprises contacting the antibody with a secondary labeled antibody conjugate.

9. The method according to claim 6, wherein the sample is from an environment.

10. The method according to claim 6, wherein the sample is obtained from an animal.

11. The method according to claim 10, wherein the animal is a mammal.

12. The method according to claim 11, wherein the mammal is a human.

13. The method according to claim 11, wherein the sample is obtained from a lung.

14. A method of detecting *Stachybotrys chartarum*, comprising:
   contacting the antibody of claim 4 with a sample; and
   detecting a complex comprising the antibody bound to an antigen from *Stachybotrys chartarum*.

15. The method according to claim 14, wherein the sample is from an environment.

16. The method according to claim 14, wherein the sample is obtained from an animal.

17. The method according to claim 14, wherein the animal is a mammal.

18. The method according to claim 17, wherein the mammal is a human.

19. The method according to claim 15, wherein the sample is obtained from a lung.

* * * * *